US 9,668,769 B2

(12) United States Patent
Kawaura et al.

(10) Patent No.: US 9,668,769 B2
(45) Date of Patent: Jun. 6, 2017

(54) TISSUE SEPARATION DEVICE

(71) Applicant: TERUMO KABUSHIKI KAISHA, Tokyo (JP)

(72) Inventors: Masakatsu Kawaura, Sunnyvale, CA (US); Shigeki Ariura, Ebina (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 69 days.

(21) Appl. No.: 14/551,831

(22) Filed: Nov. 24, 2014

(65) Prior Publication Data

US 2015/0080932 A1    Mar. 19, 2015

Related U.S. Application Data

(63) Continuation of application No. PCT/JP2013/064003, filed on May 21, 2013.

(30) Foreign Application Priority Data

May 23, 2012   (JP) ................. 2012-118037

(51) Int. Cl.
*A61B 17/34*    (2006.01)
*A61B 17/00*    (2006.01)
(Continued)

(52) U.S. Cl.
CPC ...... *A61B 17/3468* (2013.01); *A61B 17/3417* (2013.01); *A61B 2017/00805* (2013.01);
(Continued)

(58) Field of Classification Search
CPC ............ A61B 17/3417; A61B 17/3468; A61B 17/3439; A61B 17/02; A61B 17/320725;
(Continued)

(56) References Cited

U.S. PATENT DOCUMENTS 5,217,468 A * 6/1993 Clement ................ A61B 10/02
606/114
6,217,585 B1 * 4/2001 Houser ................... A61F 2/958
606/108

(Continued)

FOREIGN PATENT DOCUMENTS

| JP | 2002-541905 A | 12/2002 |
|----|---------------|---------|
| JP | 2007-160085 A | 6/2007 |
| JP | 2010-099499 A | 5/2010 |

OTHER PUBLICATIONS

International Search Report (PCT/ISA/210) mailed on Jun. 18, 2013, by the Japanese Patent Office as the International Searching Authority for International Application No. PCT/JP2013/064003.

*Primary Examiner* — Melanie Tyson
*Assistant Examiner* — Majid Jamialahmadi
(74) *Attorney, Agent, or Firm* — Buchanan Ingersoll & Rooney PC

(57) ABSTRACT

A tissue separation device includes: a sheath; a tube having a deformation part; a restriction member; and an inner structure. The tissue separation device is used in an assembled state where the tube is movably inserted in the sheath, the restriction member is inserted in the tube, and the inner structure is movably inserted in the restriction member. The inner structure includes: wires and which are expandable and contractible; an operation unit which operates expansion of the wires; a tubular body; and a traction shaft. The wires are expanded by being curved so as to protrude in opposite directions. When dissecting a biological tissue, the wires in an expanded state are moved within the tube in relation to the tube, without moving the tube relative to the living body.

20 Claims, 9 Drawing Sheets

(51) Int. Cl.
*A61F 2/00* (2006.01)
*A61B 17/32* (2006.01)

(52) U.S. Cl.
CPC .............. *A61B 2017/00986* (2013.01); *A61B 2017/320044* (2013.01); *A61B 2017/320048* (2013.01); *A61B 2017/346* (2013.01); *A61F 2/0045* (2013.01)

(58) Field of Classification Search
CPC ...... A61B 17/3421; A61B 2017/00805; A61B 2017/00986; A61B 2017/320055; A61B 2017/320048; A61B 2017/346; A61B 17/22031; A61B 17/22034; A61B 17/22035; A61F 2/0045; A61M 29/00; A61M 29/02
USPC ....... 606/185, 190, 198, 199, 191, 113, 114, 606/127, 128, 108; 604/164.1, 164.11, 604/104, 105, 106
See application file for complete search history.

(56) References Cited

U.S. PATENT DOCUMENTS

| | | | |
|---|---|---|---|
| 6,273,907 B1 | 8/2001 | Laufer | |
| 6,428,556 B1 * | 8/2002 | Chin | ................ A61B 17/00008 606/198 |
| 2004/0230206 A1 | 11/2004 | Gellman et al. | |

* cited by examiner

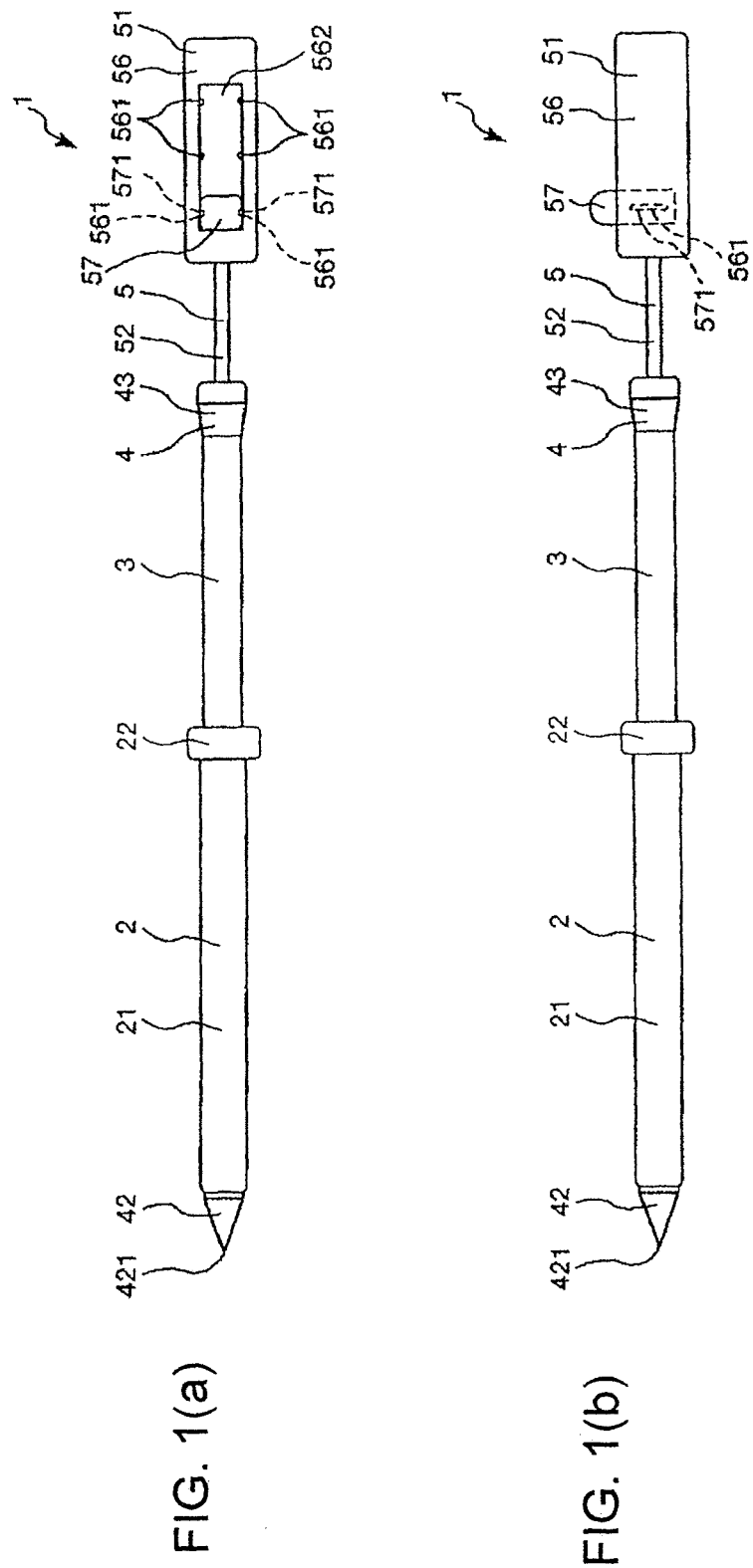

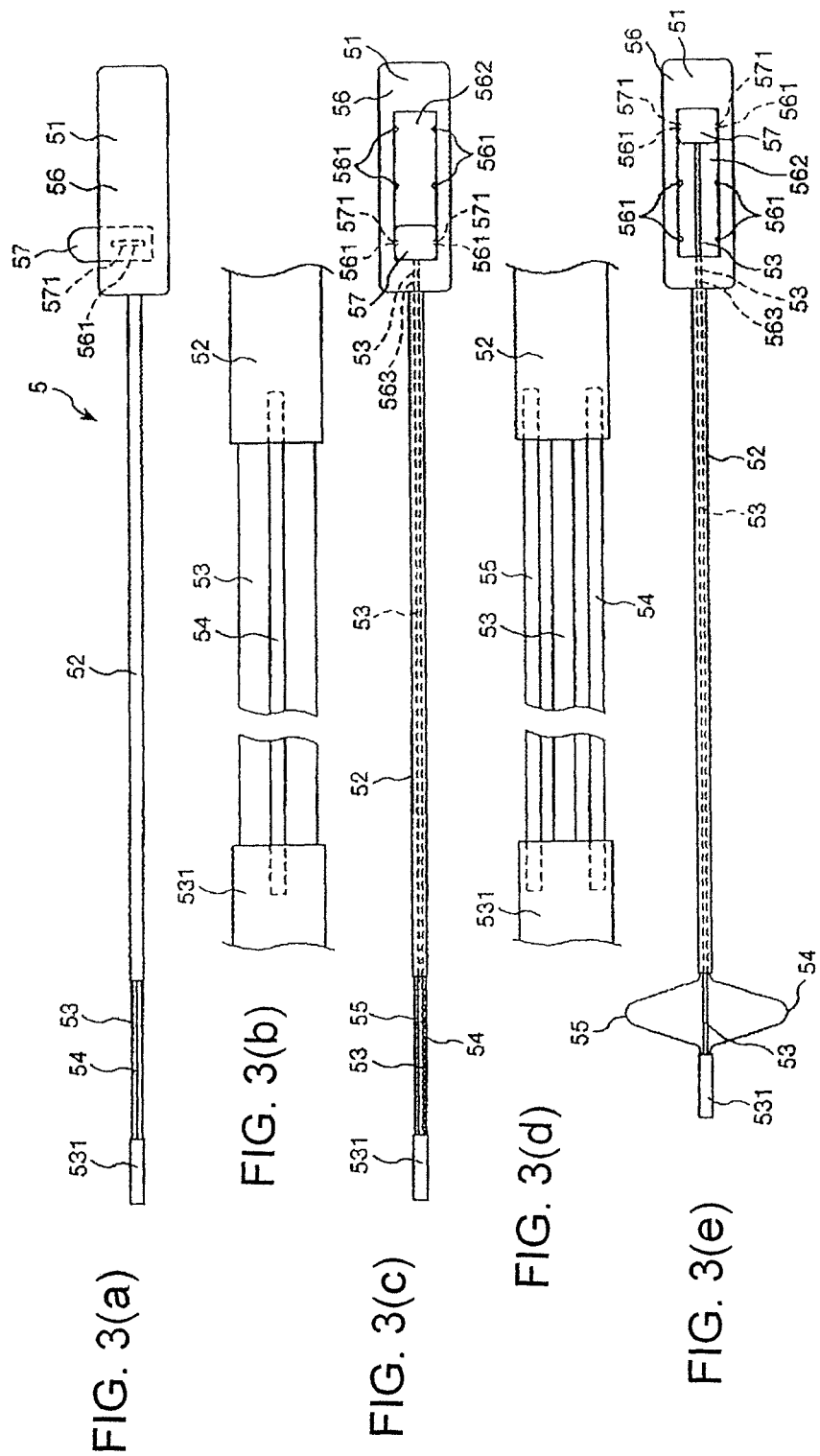

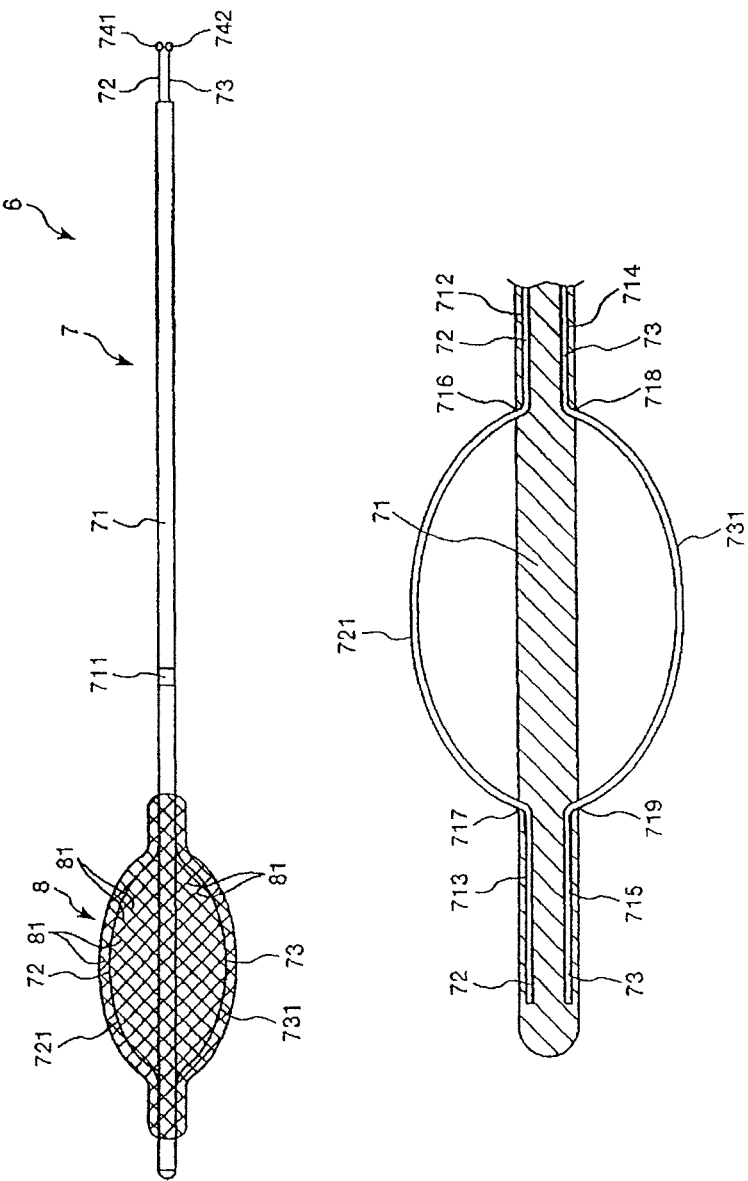

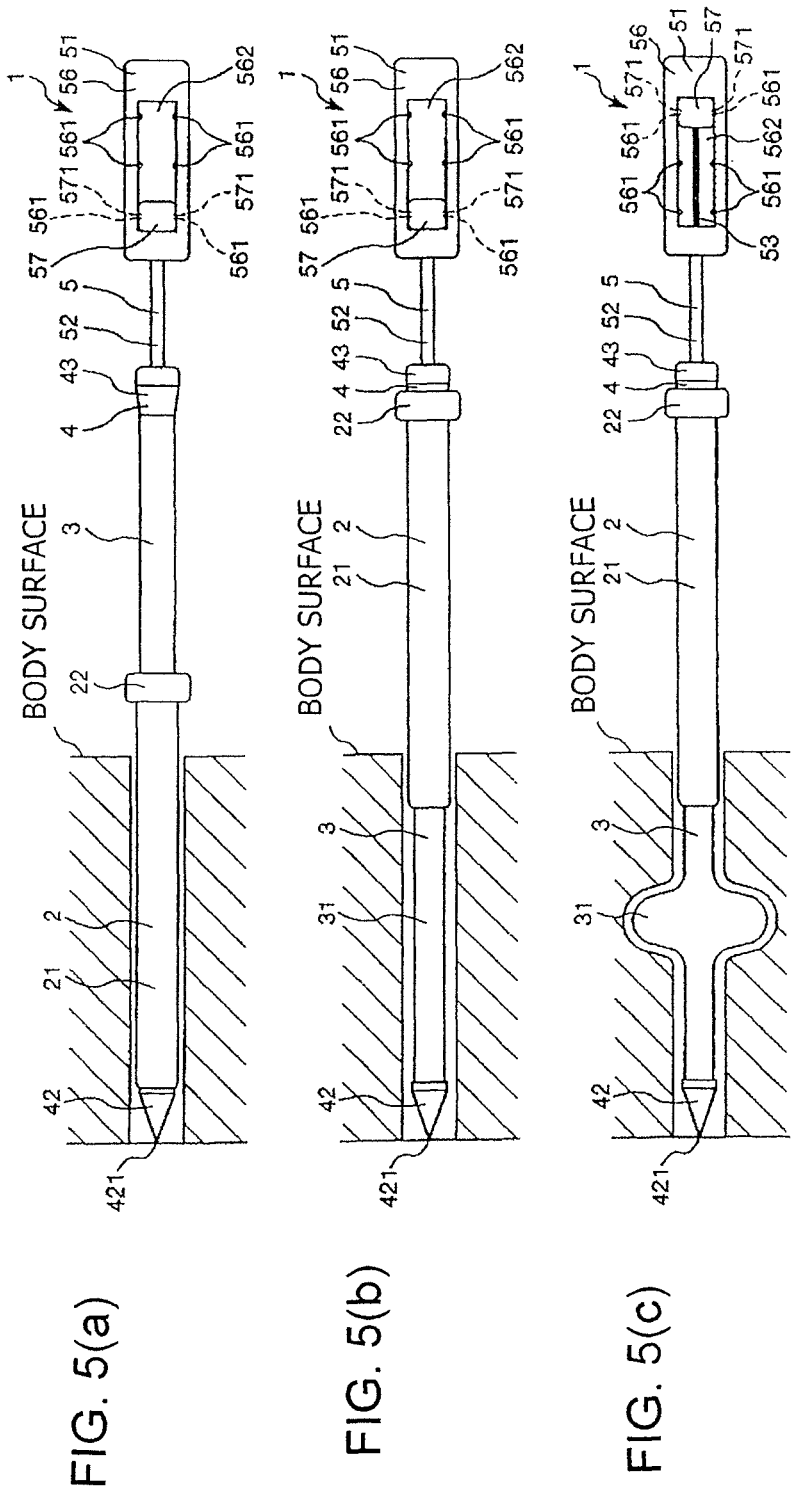

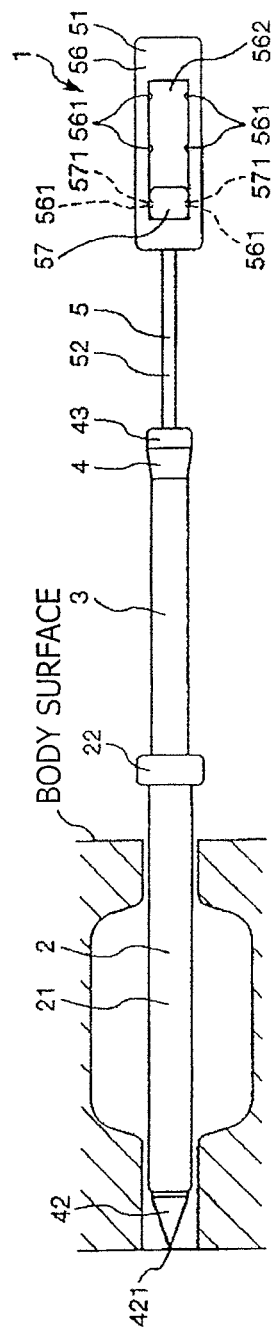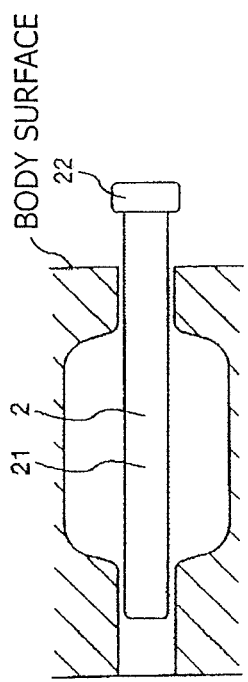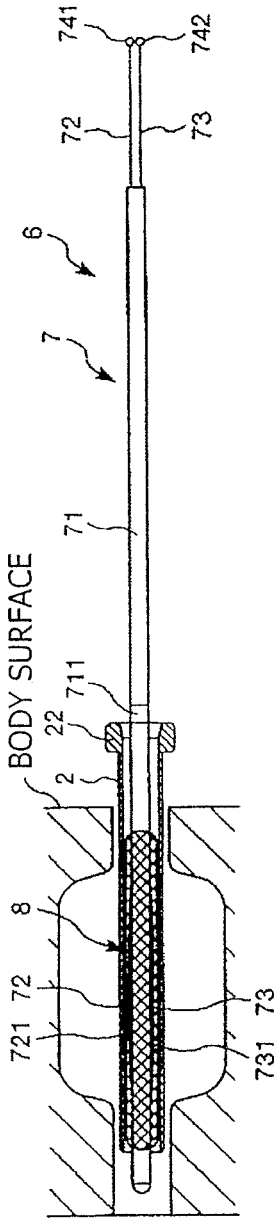
FIG. 7(a)
FIG. 7(b)
FIG. 7(c)

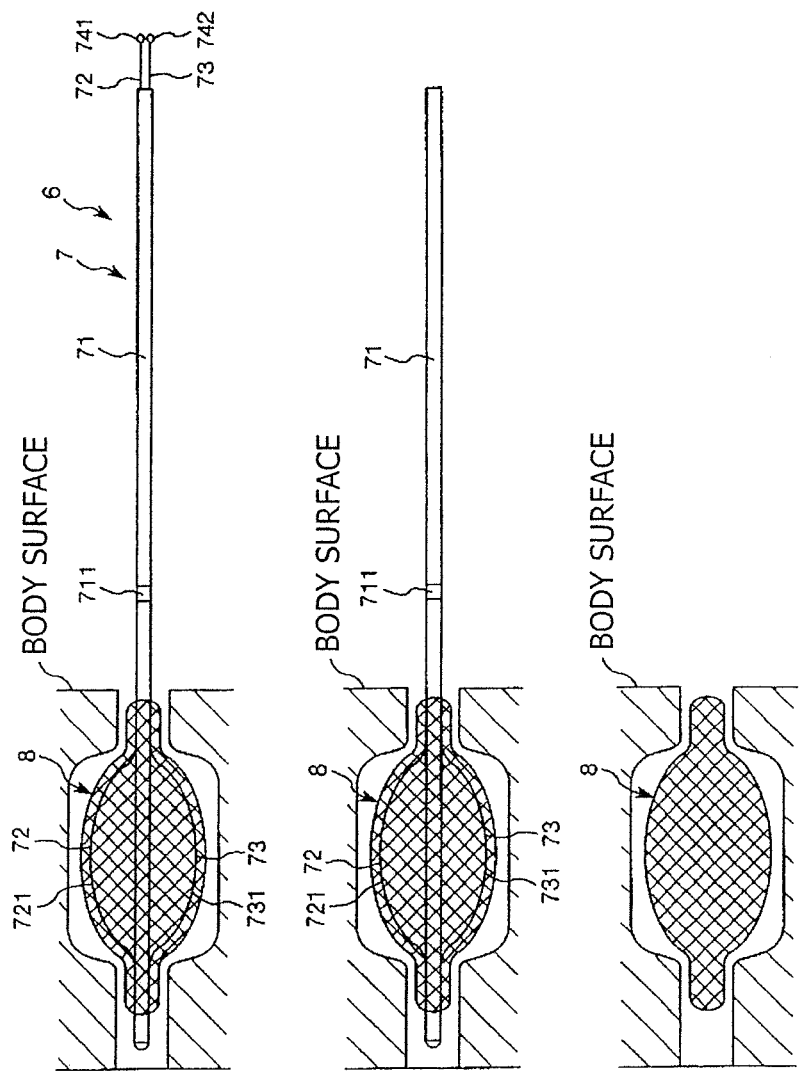

TISSUE SEPARATION DEVICE

CROSS-REFERENCES TO RELATED APPLICATIONS

This application is a continuation of International Application No. PCT/JP2013/064003 filed on May 21, 2013, and claims priority to Japanese Application No. 2012-118037 filed on May 23, 2014, the entire content of both of which is incorporated herein by reference.

TECHNICAL FIELD

The present invention generally relates to a tissue separation device.

BACKGROUND DISCUSSION

If a person suffers from a urinary incontinence, specifically if a person suffers from a stress urinary incontinence, then urine leakage can be caused by application of abdominal pressure during normal exercise or by laughing, coughing, sneezing or the like. The cause of this may be, for example, that the pelvic floor muscle which is a muscle for supporting the urethra is loosened by birth or the like.

For the treatment of urinary incontinence, a surgical treatment is effective, in which there is used, for example, a tape-shaped implant called a "sling." The sling is indwelled inside the body and the urethra is supported by the sling (see, for example, Japanese Application Publication No. 2010-99499). In order to indwell the sling inside the body, an operator would incise the vagina with a surgical knife, dissect a region between the urethra and the vagina, and make the dissected region and the outside communicate with each other through an obturator foramen using a puncture needle or the like. Then, in such a state, the sling is indwelled into the body.

In the prior art, however, it is necessary to largely incise and greatly dissect biological tissue in order to indwell the sling. This is rather invasive on the patient and leads to a heavy burden on the patient.

On the other hand, as an instrument for dissection or separation of a biological tissue, there has been proposed a dissector having an expansion part which is expandable (see, for example, Japanese Application Publication No. 2007-160085). In the dissector, the expansion part is disposed in a region for dissection or separation of a biological tissue inside the body, and thereafter the expansion part is expanded. The expansion part in the expanded state is then moved while keeping contact with the biological tissue inside the body, thereby dissecting the biological tissue.

In this dissector, however, the expansion part in the expanded state is moved while keeping contact with the biological tissue. Therefore, the friction between the expansion part and the biological tissue is great, making it difficult to smoothly dissect the biological tissue. In addition, the invasiveness to the patient is great and the burden on the patient is heavy.

SUMMARY

The tissue separation device disclosed here allows biological tissue to be dissected rather smoothly and with little burden on the patient.

According to the present invention, there is provided a tissue separation device including an inner structure including an expansion part which is expandable, and an operation unit which is disposed apart from the expansion part and which operates expansion of the expansion part and an outer structure disposed outside of the inner structure, the outer structure having a deformation part into which the expansion part is inserted, which deforms following up to a deformation of the expansion part and which is inserted into a living body, characterized in that the expansion part inserted in the deformation part and in an expanded state is moved relative to the deformation part without moving the deformation part relative to the living body.

In the tissue separation device of the present invention, preferably, the expansion part is configured to be expanded in a specified direction, and
the tissue separation device includes a restriction member restricting an expansion direction of the expansion part.

In the tissue separation device of the present invention, preferably, the restriction member is disposed between the inner structure and the outer structure.

In the tissue separation device of the present invention, preferably, the restriction member has a tubular body into which the expansion part is inserted, and the tubular body is formed at an intermediate portion thereof with a slit through which the expansion part protrudes when expanded.

In the tissue separation device of the present invention, preferably, the restriction member is provided at a distal portion thereof with a needle body having a needle tip which punctures a biological tissue.

In the tissue separation device of the present invention, preferably, the restriction member has an engaging part which engages with the outer structure and which inhibits the deformation part from moving distally relative to the restriction member.

In the tissue separation device of the present invention, preferably, the restriction member is elongated in shape and has a portion curved along a longitudinal direction thereof.

In the tissue separation device of the present invention, preferably, the inner structure has a holding part which holds a state where the expansion part is expanded.

In the tissue separation device of the present invention, preferably, the expansion part has at least one wire and is so configured as to be expanded by curving of the wire.

In the tissue separation device of the present invention, preferably, the expansion part has two wires and is so configured as to be expanded by curving of the two wires such as to protrude in opposite directions.

In the tissue separation device of the present invention, preferably, the operation unit operates to effect flexure of the wire or wires by bringing a distal-side portion and a proximal-side portion of the wire toward each other.

In the tissue separation device of the present invention, preferably, the deformation part is a tubular part which is elastically deformable.

The tissue separation device of the present invention, preferably, includes an outer tube into which the outer structure is inserted.

According to the present invention, the deformation part of the outer structure is continuously and gradually expanded along the longitudinal direction thereof, by moving the expansion part in an expanded state within the outer structure in relation to the outer structure, without moving the outer structure relative to a living body. This makes it possible to dissect a biological tissue smoothly and with low invasion, thereby alleviating the burden on the patient.

BRIEF DESCRIPTION OF DRAWINGS

FIGS. 1(a) and 1(b) are views illustrating a first embodiment of a tissue separation device representing one example of the tissue separation device disclosed here.

FIGS. 3(a)-3(e) are views illustrating an inner structure of the tissue separation device depicted in FIGS. 1(a) and 1(b).

FIGS. 4(a) and 4(b) are views illustrating an embodiment of an implant implanting instrument.

FIGS. 5(a)-5(c) are views illustrating a procedure of a technique performed by use of the tissue separation device depicted in FIGS. 1(a) and 1(b), and the implant implanting instrument depicted in FIGS. 4(a) and (b).

FIGS. 6(a)-6(c) are views illustrating the procedure performed by use of the tissue separation device depicted in FIGS. 1(a) and 1(b), and the implant implanting instrument depicted in FIGS. 4(a) and 4(b).

FIGS. 7(a)-7(c) are views illustrating the procedure performed by use of the tissue separation device depicted in FIGS. 1(a) and 1(b), and the implant implanting instrument depicted in FIGS. 4(a) and 4(b).

FIGS. 8(a)-8(c) are views illustrating the procedure performed by use of the tissue separation device depicted in FIGS. 1(a) and 1(b), and the implant implanting instrument depicted in FIGS. 4(a) and 4(b).

DETAILED DESCRIPTION

Set forth below, with reference to the accompanying drawings, is a description of embodiments of a tissue separation device representing examples of the inventive tissue separation device disclosed here.

First Embodiment

Figure 2A:
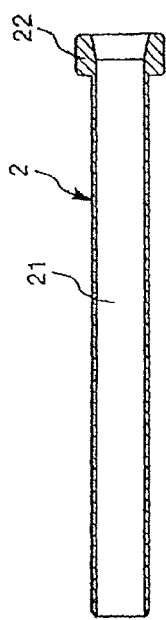
FIGS. 2(a)-2(c) are views depicting members of the tissue separation device depicted in FIGS. 1(a) and 1(b).
Figure 2B:
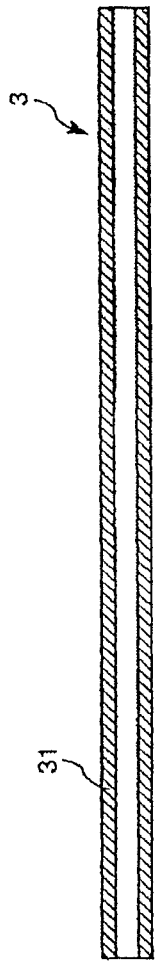
Figure 2C:
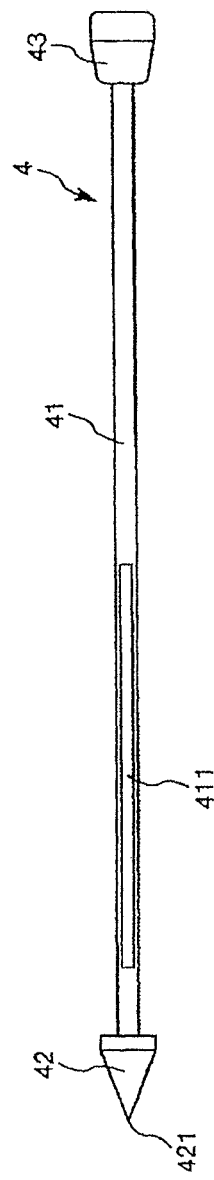

FIGS. 1(a) and 1(b) (collectively referred to as FIG. 1) illustrate a first embodiment of the tissue separation device, wherein FIG. 1(a) is a plan view and FIG. 1(b) is a side view. FIGS. 2(a)-2(c) (collectively referred to as FIG. 2) depict members of the tissue separation device depicted in FIGS. 1(a) and 1(b), wherein FIG. 2(a) is a side view showing a sheath, FIG. 2(b) is a side view showing a tube, and FIG. 2(c) is a side view showing a restriction member. FIGS. 3(a)-3(e) (collectively referred to as FIG. 3) illustrate an inner structure of the tissue separation device depicted in FIG. 1, wherein FIG. 3(a) is a side view, FIG. 3(b) is a side view showing the vicinity of a wire in a magnified form, FIG. 3(c) is a plan view, FIG. 3(d) is a plan view showing the vicinity of the wire in a magnified form, and FIG. 3(e) is a plan view showing a state where the wire of the inner structure is expanded. FIGS. 4(a)-4(b) (collectively referred to as FIG. 4) illustrate an embodiment of an implant implanting instrument, wherein FIG. 4(a) is a plan view, and FIG. 4(b) is a sectional view depicting a shaft and the wires at a distal portion of the implant implanting instrument. FIGS. 5(a)-5(c) (collectively referred to as FIG. 5), FIGS. 6(a)-6(c) (collectively referred to as FIG. 6), FIGS. 7(a)-7(c) (collectively referred to as FIG. 7), and FIGS. 8(a)-8(c) (collectively referred to as FIG. 8) show views explaining a procedure performed by use of the tissue separation device depicted in FIGS. 1(a) and 1(b) and the implant implanting instrument depicted in FIGS. 4(a) and 4(b).

In the following description, the left side in FIGS. 1 to 8 will be referred to as the "distal end," the right side in the figures will be referred to as the "proximal end," the upper side in FIGS. 1(b) and 3(a) will be referred to as "upper (side)," and the lower side in the figures will be referred to as "lower (side)." In addition, for easy visibility of the figures and illustrated features, the magnifications of each part in FIG. 3(a) and in FIG. 3(b), the magnifications of each part in FIG. 3(c) and in FIG. 3(d), and the magnifications of each part in FIG. 4(a) and in FIG. 4(b) may not be equal.

A tissue separation device 1 shown in these figures is a device for use in treatment of female urinary incontinence, in other words, in implanting into a living body an implant for treatment of urinary incontinence. Specifically, the tissue separation device 1 in this embodiment is a device for dissecting a biological tissue in a region an implant is implanted between a urethra and a vagina. A puncture hole extending from the surface of the body to reach a region between the urethra and the vagina is formed by the tissue separation device 1.

In addition, the implant is an instrument which is implantable for treatment of female urinary incontinence. Specifically, the implant is an instrument which is implanted in a living body to support a urethra (biological tissue), for example, an instrument which supports the urethra tension-free or in the manner of pulling the urethra in a direction for spacing away from a vaginal wall when the urethra would otherwise be going to move toward the vaginal wall. As the implant, there can be used, for example, a flexible member, which may be an elongated member or may be a comparatively short member.

First of all, the tissue separation device 1 will be described.

As shown in FIGS. 1 to 3, the tissue separation device 1 includes: a sheath 2 as an outer tube; a tube 3 as an outer structure which is elongated in shape; a restriction member 4 which is elongated in shape; and an inner structure 5 which is elongated in shape. The tissue separation device 1 is used in an assembled state in which the sheath 2, the tube 3, the restriction member 4, and the inner structure 5 are assembled together, as shown in FIG. 1. In the assembled state, the tube 3 is movably inserted in the sheath 2, the restriction member 4 is inserted in the tube 3, and the inner structure 5 is movably inserted in the restriction member 4.

The inner structure 5 includes: two wires 54 and 55 as (expandable) expansion parts which are disposed at a distal portion of the inner structure 5 and are expandable and contractible; an operation unit 51 which is disposed at a position spaced apart from the two wires 54 and 55, specifically, at a proximal portion of the inner structure 5, and which operates expansion of the wires 54 and 55; a tubular body 52; and a traction shaft 53 which is inserted (positioned) in the tubular body 52 and is disposed to be movable relative to the tubular body 52 along the longitudinal direction of the tubular body 52.

The operation unit 51 includes: a main body part 56 fixed to a proximal portion of the tubular body 52; and a lever 57 disposed to be movable relative to the main body part 56 along the longitudinal direction of the inner structure 5. The operation unit 51 operates to expand each of the wires 54 and 55 (which will be described later) through effecting flexure of the wire by bringing a distal-side portion and a proximal-side portion of the wire toward each other, and to contract each of the wires 54 and 55 through pulling the wire by bringing the distal-side portion and the proximal-side portion of the wire away from each other.

The shape of the main body part 56 is not specifically restricted; in this embodiment, the main body part 56 has a rectangular parallelepiped shape. The main body part 56 includes, in an upper portion of the main body part 56 in FIG. 1(a), a groove 562 which extends along the longitudinal direction of the inner structure 5.

The lever 57 is disposed inside the groove 562 so as to be movable along the groove 562. An upper portion, in FIG.

3(*a*), of the lever 57 protrudes upward to above an upper surface, in FIG. 3(*a*), of the main body part 56.

In addition, the lever 57 is formed with or includes a pair of grooves 571. The grooves 571 are formed or located in side surfaces, on the face side and the back side in regard to the sheet surface of FIG. 3(*a*), of the lever 57. The side surfaces of the groove 562 inside the groove 562 of the main body part 56 are formed with or include three pairs of ribs 561, each pair of ribs 561 being configured to engage the pair of grooves 571. The three pairs of ribs 561 are arranged at regular intervals along the longitudinal direction of the groove 562. The lever 57 is held onto or relative to the main body part 56 when the ribs 561 are positioned in the grooves 571 so that the grooves 571 and ribs 561 are in engagement with each other. The grooves 571 and the ribs 561 constitute a holding part which holds a state in which the wires 54 and 55 are expanded.

A proximal portion of the tubular body 52 is fixed to a distal portion of the main body part 56 of the operation unit 51, and the main body part 56 is formed with or includes a through-hole 563 in the region of the main body part 56 where the tubular body 52 is fixed (see FIGS. 3(*c*) and 3(*e*)). A distal portion of the through-hole 563 communicates with the lumen of the tubular body 52, while a proximal portion of the through-hole 563 communicates with the inside of the groove 562.

In addition, the shape of the tubular body 52 is not specifically restricted; in this embodiment, the tubular body 52 has a rectilinear shape, and its outer shape in transverse cross section is a circle. The cross-sectional shape of the lumen of the tubular body 52 is a shape corresponding to the cross-sectional shape of the traction shaft 53; namely, it is a tetragonal shape.

The traction shaft 53 is fixed at its proximal portion to the lever 57 of the operation unit 51, in the state of being inserted in the tubular body 52 and having its distal portion protruding distally beyond the distal end of the tubular body 52. This ensures that a moving operation of the lever 57, namely, a movement of the lever 57 along the longitudinal direction of the groove 562, moves the traction shaft 53 relative to the tubular body 52 along the longitudinal direction of the inner structure 5, together with the lever 57. In addition, by virtue of the engagement between the grooves 571 of the lever 57 and the ribs 561 of the main body part 56, the lever 57 is held onto the main body part 56, whereby the positional relationship between the traction shaft 53 and the tubular body 52 is fixed.

In addition, the traction shaft 53 is provided at its distal portion with a fixation part 531 for fixation of the wires 54 and 55. The fixation part 531 is configured or sized to have an outer dimension (outer diameter) greater than that portion of the traction shaft 53 which is located proximally of the fixation part 531.

The shape of the traction shaft 53 is not particularly limited. In this embodiment, the traction shaft 53 has a rectilinear shape, and that portion of the traction shaft 53 which is located proximally of the fixation part 531 is tetragonal in cross-sectional shape. This makes it possible to prevent the traction shaft 53 from rotating relative to the tubular body 52.

In addition, the shape of the fixation part 531 is not specifically restricted; in this embodiment, it is a cylindrical shape. The outside diameter of the fixation part 531 is equal to the outside diameter of the tubular body 52. Note that, naturally, the outside diameter of the fixation part 531 may be smaller or greater than the outside diameter of the tubular body 52.

The wires 54 and 55 are each disposed along the longitudinal direction of the inner structure 5. In addition, the wires 54 and 55 are spaced apart from each other and are so disposed as to face each other, with the center axis of the inner structure 5 interposed between the two wires 54, 55. Distal portions of the wires 54 and 55 are individually fixed to a proximal portion of the fixation part 531, while being inserted or positioned in a hole which extends distally along the longitudinal direction of the inner structure 5 from a proximal end face of the fixation part 531 of the traction shaft 53. Proximal portions of the wires 54 and 55 are each fixed to a distal portion of the tubular body 52, while being inserted or positioned in a hole which extends proximally along the longitudinal direction of the inner structure 5 from a distal end face of the tubular body 52. These wires 54 and 55 are individually configured to be expanded in a specified direction, specifically, in a direction from the center axis of the inner structure 5 toward an outer side (i.e., outward in diametrically opposite directions as shown in FIG. 3(*e*)).

Here, a state as shown in FIGS. 3(*a*) to 3(*d*) is a state in which the wires 54 and 55 are contracted, namely, a contracted state, whereas a state as shown in FIG. 3(*e*) is a state in which the wires 54 and 55 are expanded, namely, an expanded state.

In the state where the wires 54 and 55 are contracted as shown in FIGS. 3(*a*) to 3(*d*), the wires 54 and 55 are disposed along the longitudinal direction of the inner structure 5 so that they are parallel to each other. In addition, when the inner structure 5 is viewed in the longitudinal direction of the inner structure 5, the wires 54 and 55 are located on the inside as compared with the fixation part 531 and the tubular body 52.

In the state where the wires 54 and 55 are expanded as shown in FIG. 3(*e*), the wires 54 and 55 are so curved as to protrude in opposite directions, with the center axis of the inner structure 5 between the two wires 54, 55. This helps ensure that the wires 54 and 55 are both expanded in the same plane.

In addition, the material constituting the wires 54 and 55 is not specifically restricted; examples of the material usable here include superelastic alloys such as Ni—Ti alloys.

The restriction member 4 is disposed between the tube 3 and the inner structure 5 in the assembled state, and has a function of restricting the expansion directions of the wires 54 and 55.

As shown in FIG. 2(*c*), the restriction member 4 includes: a main body part 41 including a tubular body; a needle body 42 provided at a distal portion of the main body part 41 and having a sharp needle tip 421 configured to puncture a biological tissue; and a hub 43 provided at a proximal portion of the main body part 41. The restriction member 4 has rigidity.

The shape of the main body part 41 is not particularly limited. In this embodiment, the main body part 41 has a rectilinear shape, and its external and internal shapes in cross section are individually a circle.

The main body part 41 is formed, at an intermediate portion of the main body part (in this embodiment, at a portion ranging from a central portion to a distal portion of the main body part 41), with a pair of slits 411 extending along the longitudinal direction of the main body part 41. The slits 411 are so disposed as to face each other, with the center axis of the main body part 41 interposed between the two slits 411. In the assembled state, the wires 54 and 55 are inserted or positioned in the main body part 41 and are disposed in the positions of the slits 411. This helps ensure that when the wires 54 and 55 are expanded, the wires 54 and 55 protrude via the slits 411 to outside of the main body part 41. In this instance, besides, the expansion directions of the wires 54 and 55 are restricted by the respective slits 411, so that the wires 54 and 55 are reliably expanded in the same plane.

In the assembled state, the needle body 42 protrudes distally from the distal end of the tube 3. The shape of the needle body 42 is not specifically restricted. In this embodiment, a proximal portion of the needle body 42 has a cylindrical shape, and a portion located distally of the proximal portion is conical in shape.

In addition, the outside diameter of the proximal portion of the needle body 42 is greater than the outside diameter of a distal portion of the main body part 41. In the assembled state, the proximal portion of the needle body 42 is in engagement with a distal portion of the tube 3. This inhibits the tube 3 from moving distally relative to the restriction member 4. Therefore, the proximal portion of the needle body 42 constitutes an engaging part which inhibits a deformation part 31 (described later) of the tube 3 from moving distally relative to the restriction member 4.

The tube 3 shown in FIG. 2(b) includes a tubular body which is elastically deformable. An elastically deformable tubular part, as an intermediate portion of the tube 3 (in this embodiment, a distal-side portion of the tube 3), constitutes the deformation part 31. In the assembled state, the wires 54 and 55 are inserted or positioned in the deformation part 31 by way of the restriction member 4. The deformation part 31 deforms by pulling the wires 54 and 55; specifically, the deformation part 31 expands or contracts as a result of expansion or contraction of the wires 54 and 55. At least the deformation part 31 of the tube 3 is inserted in a living body when used.

In addition, the shape of the tube 3 is not particularly limited. In this embodiment, the tube 3 has a rectilinear shape, and its external and internal shapes in cross section are individually a circle.

As shown in FIG. 2(a), the sheath 2 includes: a main body part 21 including a tubular body; and a hub 22 provided at a proximal portion of the main body part 21.

In the assembled state, the sheath 2 is so disposed that its distal portion is located at a distal portion of the restriction member 4 and that the needle body 42 protrudes distally from the distal end of the sheath 2.

The shape of the main body part 21 is not specifically restricted. In this embodiment, the main body part 21 has a rectilinear shape, and its external and internal shapes in cross section are individually a circle.

In addition, the length of the sheath 2 is smaller than the length of the main body part 41 of the restriction member 4, and is so set that the slits 411 can be covered with the sheath 2 and that, when the sheath 2 is moved to a proximal portion of the restriction member 4, at least the deformation part 31 of the tube 3 is exposed.

Now, an embodiment of an implant implanting instrument will be described below.

As shown in FIG. 4, an implant implanting instrument 6 includes: an implant 8; and an implanting instrument main body 7 which holds the implant 8 in a freely detachable manner (detachably). The implant implanting instrument 6 is an instrument which is inserted into a puncture hole formed in a living body by the tissue separation device 1 and by which the implant 8 is implanted in a region between a urethra and a vagina dissected by the tissue separation device 1.

The implant 8 is called "sling" and, in this embodiment, it is flat-shaped. In addition, the implant 8 is net-like in form and, in this embodiment, it includes a body knitted in a net form (lattice form) by intersection of filamentous elements 81, in other words, includes a net-like knitting. Examples of the filamentous element 81 include those which are circular in cross-sectional shape, and those which are flat in cross-sectional shape, namely, which are band-like (ribbon-like) in shape.

In addition, the diameter of the filamentous element 81 constituting the implant 8 is not particularly limited, and is preferably about 0.05 to 1.0 mm, more preferably about 0.2 to 0.6 mm.

The material constituting the implant 8 is not specifically restricted; examples of the material usable here include various biocompatible resin materials (such as polypropylene), their fibers and the like.

Note that, naturally, the implant 8 is not restricted to net-like implants.

The implanting instrument main body 7 includes: a shaft 71; and two wires 72 and 73 disposed on the shaft 71. The implanting instrument main body 7 supports the implant 8 in a freely detachable manner at an intermediate portion of the shaft 71 (in this embodiment, at a distal portion of the shaft 71).

In this embodiment, the shaft 71 has a rectilinear shape, and its external shape in cross section is a circle.

The shape of the shaft 71 is not restricted to the just-mentioned; for example, the external shape in cross section may be an ellipse. In addition, for example in the case where the tissue separation device 1 has a portion curved along the longitudinal direction of the tissue separation device 1 and where the puncture hole formed in a living body by the tissue separation device 1 has a portion curved along the longitudinal direction of the tissue separation device 1, as in a second embodiment described later, the shaft 71 preferably has a portion curved along the longitudinal direction of the shaft 71. In this case, the curved shape of the shaft 71 preferably corresponds to the curved shape of the tissue separation device 1, and examples of the curved shape include circular arcs and elliptical arcs.

A distal end portion of the shaft 71 is rounded. This helps ensure that the shaft 71 can be smoothly inserted into a living body, and the safety of the patient can be enhanced.

In addition, the shaft 71 is formed, in positions eccentric with respect to the center axis of the shaft 71 and along the longitudinal direction of the shaft 71, with lumens 712 and 713 in which the wire 72 is to be inserted or positioned. The shaft 71 is formed, in positions eccentric with respect to the center axis of the shaft 71 and on the opposite side of the center axis of the shaft 71 from the lumens 712 and 713 and along the longitudinal direction of the shaft 71, with lumens 714 and 715 in which the wire 73 is to be inserted.

The lumen 712 is formed to extend from the proximal end to a distal portion of the shaft 71, and is open at the proximal end of the shaft 71. In addition, a side wall of the shaft 71 is formed, at its portion corresponding to a distal portion of the lumen 712, with a side hole 716 communicating with the distal portion of the lumen 712. This side hole 716 is inclined so that its distal-side portion is located on the side of the outer circumference of the shaft 71 as compared with its proximal-side portion.

The lumen 713 is formed on the distal side of the lumen 712 and on an extension line of the lumen 712 (the lumens 712, 713 are coaxial), so as to be spaced by a predetermined distance from a distal portion of the lumen 712. The lumen 713 is closed at its distal end. In addition, the side wall of the shaft 71 is formed, at its portion corresponding to a proximal portion of the lumen 713, with a side hole 717 communicating with the proximal portion of the lumen 713. This side hole 717 is inclined so that its proximal-side portion is located on the side of the outer circumference of the shaft 71 as compared with its distal-side portion.

The lumen 714 is formed to extend from the proximal end to a distal portion of the shaft 71, and is open at the proximal end of the shaft 71. In addition, the side wall of the shaft 71 is formed, at its portion corresponding to a distal portion of the lumen 714, with a side hole 718 communicating with the distal portion of the lumen 714. This side hole 718 is inclined so that its distal-side portion is located on the side of the outer circumference of the shaft 71 as compared with its proximal-side portion.

The lumen 715 is formed on the distal side of the lumen 714 and on an extension line of the lumen 714 (the lumens 714, 715 are coaxial), so as to be spaced by a predetermined distance from a distal portion of the lumen 714. The lumen 715 is closed at its distal end. In addition, the side wall of the shaft 71 is formed, at its portion corresponding to a proximal portion of the lumen 715, with a side hole 719 communicating with the proximal portion of the lumen 715. This side hole 719 is inclined so that its proximal-side portion is located on the side of the outer circumference of the shaft 71 as compared with its distal-side portion.

The shaft 71 is provided with a marker 711 at an intermediate portion of the shaft 71. The marker 711, when inserting the implant implanting instrument 6 into a puncture hole formed in a living body, indicates how much the implant implanting instrument 6 should be inserted. In this embodiment, the position of the marker 711 is so set that the insertion depth of the implant implanting instrument 6 into the puncture hole will be appropriate when the marker 711 is positioned at the proximal end of the sheath 2 (see FIG. 7(c)). In other words, a curved portion 721 of the wire 72, a curved portion 731 of the wire 73 (which curved portions are to be described later), and the implant 8 are located in a region where to implant the implant 8 between a urethra and a vagina dissected by the tissue separation device 1, at the time when the marker 711 is positioned at the proximal end of the sheath 2.

The wires 72 and 73 are both elastic.

An intermediate portion of the wire 72 (in this embodiment, a distal portion of the wire 72) is curved so as to correspond to the external shape of the implant 8. In other words, the distal portion of the wire 72 is formed with or includes a curved portion 721 having a shape corresponding to the external shape of the implant 8.

The wire 72 is shaped in this fashion when in a natural state where no external force is exerted on the wire 72; in this state, the curved portion 721 protrudes to the exterior via the side holes 716 and 717. In addition, a proximal portion of the wire 72 protrudes proximally from the proximal end of the shaft 71.

A grasping part 741 is fixed to a proximal portion of the wire 72. This grasping part 741 is a part to be grasped when pulling the wire 72 out of the shaft 71; in this embodiment, the grasping part 741 is spherical in shape.

Similarly, an intermediate portion of the wire 73 (in this embodiment, a distal portion of the wire 73) is curved so as to correspond to the external shape of the implant 8. In other words, the distal portion of the wire 73 is formed with or includes the curved portion 731 having a shape corresponding to the external shape of the implant 8.

This wire 73 is shaped in this fashion when in a natural state where no external force is exerted on the wire 73; in this state, the curved portion 731 protrudes to the exterior via the side holes 718 and 719. In addition, a proximal portion of the wire 73 protrudes proximally from the proximal end of the shaft 71.

A grasping part 742 is fixed to a proximal portion of the wire 73. The grasping part 742 is a part to be grasped when pulling the wire 73 out of the shaft 71; in this embodiment, the grasping part 742 is spherical in shape.

In addition, the material constituting the wires 72 and 73 is not particularly limited. Examples of the material usable here include superelastic alloys such as Ni—Ti alloys.

The implant 8 is freely detachably held on the curved portion 721 of the wire 72 and the curved portion 731 of the wire 73. In this embodiment, the curved portions 721 and 731 each alternately pass the face side and the back side, in regard to the sheet surface of FIG. 4, of the filamentous elements 81 of the implant 8, thereby holding the implant 8. That is, the curved portions 721, 731 of the wires 72, 73 are woven between the back side and the front side of the implant 8.

When the wires 72 and 73 are pulled out of the implant 8 by grasping the grasping parts 741 and 742 and pulling the wires 72 and 73 proximally, the implant 8 is detached from the implanting instrument main body 7, in other words, from the wires 72 and 73.

Now, an example of the method of using the tissue separation device 1 and the implant implanting instrument 6 will be described below. Here, a procedure up to implanting of the implant 8 (for treatment of female urinary incontinence) into a living body by use of the tissue separation device 1 and the implant implanting instrument 6 will be described.

First, as shown in FIG. 5(a), the tissue separation device 1 in the assembled state is used to puncture a patient's body from the patient's body surface. In this case, the deformation part 31 of the tube 3 is disposed in a region where the implant 8 is to be implanted between the urethra and the vagina. In an initial state, the lever 57 of the operation unit 51 is located on the most distal side in the groove 562 of the main body part 56, and the grooves 571 of the lever 57 engage with the most distally located ribs 561 on the most distal side of the main body part 56, whereby the lever 57 is held onto or with respect to the main body part 56.

Next, as shown in FIG. 5(b), the sheath 2 is moved proximally, to fit the hub 22 of the sheath 2 and the hub 43 of the restriction member 4 to each other, whereby the deformation part 31 of the tube 3 is exposed.

Subsequently, as shown in FIG. 5(c), the lever 57 of the operation unit 51 is moved proximally. As a result, the traction shaft 53 is moved proximally together with the lever 57 in relation to the tubular body 52, and the wires 54 and 55 are individually bent (outwardly deformed), to protrude via the slits 411 of the restriction member 4 to the exterior. In other words, the respective wires 54 and 55 are curved so as to protrude in opposite directions, with the center axis of the inner structure 5 interposed the two wires 54, 55, and to be expanded in the same plane (see FIG. 3(e)). The deformation part 31 of the tube 3 is outwardly expanded outwardly as a result of the expansion of the wires 54 and 55. That is, the outward expansion of the wires 54, 55 causes the deformation part 31 of the tube 3 to also outwardly expand. In addition, the lever 57 is moved to the most proximal side within the groove 562 of the main body part 56, and the grooves 571 of the lever 57 engage with the most proximally located ribs 561 on the most proximal side of the main body part 56, whereby the lever 57 is held onto or with respect to the main body part 56.

Figures 6A, 6B, 6C:
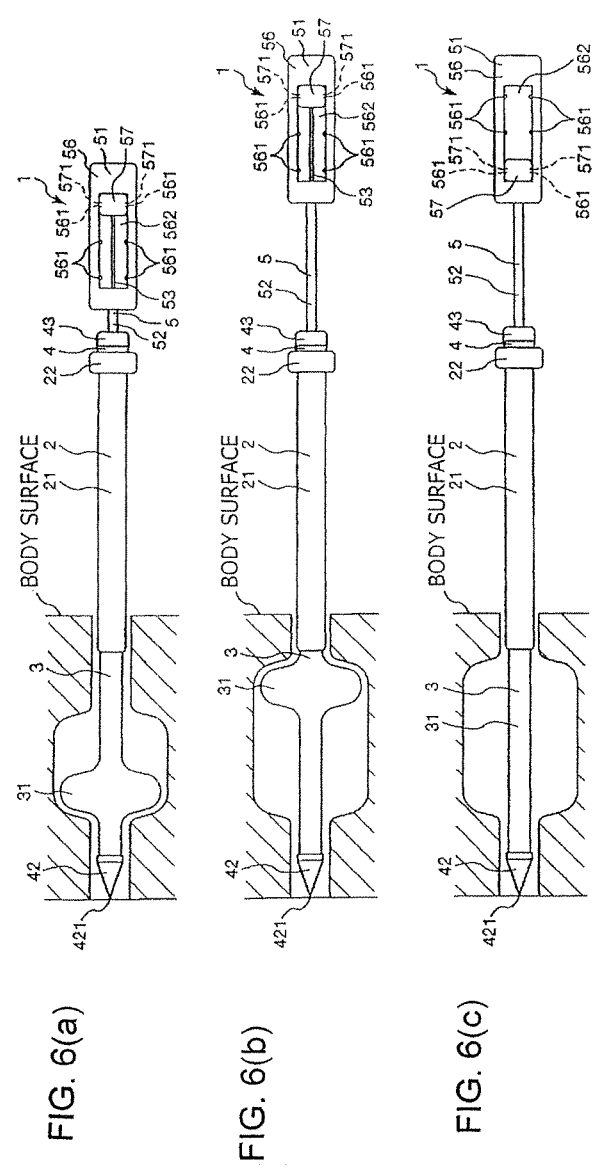

Next, as shown in FIG. 6(a), while holding the sheath 2 and the restriction member 4, the operation unit 51 is moved distally relative to the restriction member 4 and the tube 3. It follows that the wires 54 and 55 in the expanded state are moved distally within the tube 3 in relation to the restriction member 4 and the tube 3, while the sheath 2, the restriction member 4, and the tube 3 are kept unmoved in relation to the living body. With the wires 54 and 55 in the expanded state moved distally within the tube 3, the deformation part 31 of the tube 3 is distally continuously and gradually expanded along the longitudinal direction of the tube 3, whereby a biological tissue between the urethra and the vagina is separated.

Subsequently, as shown in FIG. 6(b), while holding the sheath 2 and the restriction member 4, the operation unit 51 is moved proximally relative to the restriction member 4 and the tube 3. If follows that the wires 54 and 55 in the expanded state are moved proximally within the tube 3 in relation to the restriction member 4, and the tube 3, while the sheath 2, the restriction member 4, and the tube 3 are kept unmoved in relation to the living body. With the wires 54 and 55 in the expanded state moved proximally within the tube 3, the deformation part 31 of the tube 3 is proximally continuously and gradually expanded along the longitudinal direction of the tube, whereby the biological tissue between the urethra and the vagina is separated.

Next, as shown in FIG. 6(c), the lever 57 of the operation unit 51 is moved distally. As a result, the traction shaft 53 is moved distally together with the lever 57 in relation to the tubular body 52, and the wires 54 and 55 are individually contracted, in other words, they are disposed along the longitudinal direction of the inner structure 5 so as to become parallel to each other (see FIGS. 3(a) to 3(d)). The deformation part 31 of the tube 3 also contracts as a result of the contraction of the wires 54 and 55. In addition, the lever 57 is moved to the most distal side within the groove 562 of the main body part 56, and the grooves 571 of the lever 57 engage with the most distal ribs 561 on the most distal side of the main body part 56, whereby the lever 57 is held onto or relative to the main body part 56.

By these operating steps, a puncture hole extending from the body surface to a region between the urethra and the vagina is formed, and a space in which to implant the implant 8 is formed between the urethra and the vagina.

Subsequently, as shown in FIG. 7(a), the sheath 2 is moved distally until its distal end portion is positioned at a proximal end portion of the needle body 42 of the restriction member 4.

Next, as shown in FIG. 7(b), the inner structure 5, the tube 3, and the restriction member 4 are pulled out, leaving the sheath 2 alone.

Subsequently, as shown in FIG. 7(c), the implant implanting instrument 6 is inserted into the sheath 2, its distal end first. In this case, it is ensured that the marker 711 on the implant implanting instrument 6 is positioned at the proximal end of the sheath 2. As a result, the implant 8 is disposed in the position of the space where to implant the implant 8, which space has been formed by the tissue separation device 1.

Next, as shown in FIG. 8(a), the sheath 2 is pulled out.

Subsequently, as shown in FIG. 8(b), with the grasping parts 741 and 742 grasped, the wires 72 and 73 are individually pulled out of the shaft. This renders the implant 8 detachable from the implanting instrument main body 7. That is, the implant 8 is detached or separated from, and no longer held by, the implanting instrument main body 7.

Next, as shown in FIG. 8(c), the shaft 71 is pulled out, and a predetermined treatment is performed, to complete the manual procedure. By the above operating steps, the implant 8 is implanted between the urethra and the vagina.

As has been described above, according to the tissue separation device 1, it is possible, at the time of implanting an implant 8, to dissect the biological tissue in the region where to implant the implant 8 between the urethra and the vagina, and thus create a space or region for the implant, by only forming a comparatively small puncture hole in the living body. In addition, the implant can be implanted through only a relatively low invasive manual procedure, without the need to perform high invasive incision or the like, so that the burden on the patient is slight. The safety of the patient is also maintained.

In addition, the implant 8 is flat-shaped, and the tissue separation device 1 forms a flat-shaped space in a living body by dissecting a biological tissue by the wires 54 and 55 expanded in the same plane. Therefore, the space where to implant the implant 8 can be formed by minimal dissection or separation of tissue, which promises lessened invasion.

At the time of dissecting the biological tissue in the region where the implant 8 is to be implanted between the urethra and the vagina, the wires 54 and 55 in an expanded state are moved within the tube 3 in relation to the tube 3, without moving the tube 3 relative to the living body, whereby the deformation part 31 of the tube 3 is continuously and gradually expanded along the longitudinal direction thereof. This makes it possible to dissect the biological tissue rather smoothly and with relatively low invasion, thereby alleviating the burden on the patient.

In addition, since the wires 54 and 55 are inserted in the deformation part 31 of the tube 3, the wires 54 and 55 can be prevented from being caught on the biological tissue when the wires 54 and 55 are moved.

Because the expansion directions of the wires 54 and 55 are restricted by the restriction member 4 and the expansion directions are known beforehand, the biological tissue can be dissected using the wires 54 and 55 without damaging the urethra or the vagina.

Second Embodiment

Figure 9:
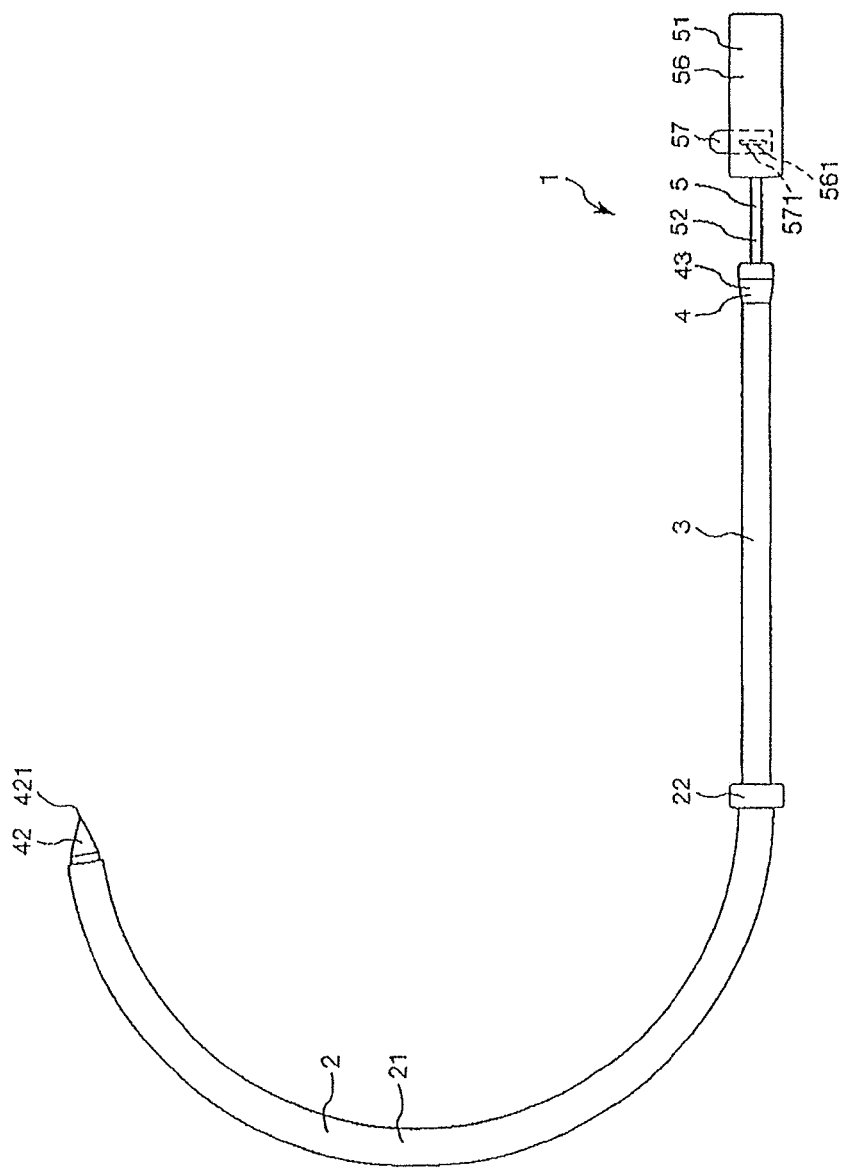
FIG. 9 is a side view illustrating a second embodiment of the tissue separation device representing another example of the tissue separation device disclosed here.

FIG. 9 is a side view illustrating a second embodiment of the tissue separation device representing another example of the device disclosed here. In the following description, the operator's hand side in FIG. 9 will be referred to as the "proximal end," and the side opposite to the hand side along the longitudinal direction of the tissue separation device will be referred to as the "distal end."

The following description of the second embodiment will center on differences between this embodiment and the above-described first embodiment. Features in this second embodiment that are the same as in the first embodiment are identified by common reference numerals and a detailed description of such features is not repeated As shown in FIG. 9, a tissue separation device 1 according to the second embodiment has a portion curved in a circular arc shape along the longitudinal direction of the device. In the configuration shown in the figure, the tissue separation device 1 is curved in its part ranging from an intermediate portion to a distal portion in the longitudinal direction.

In this case, a restriction member 4 is curved in a natural state, whereas a sheath 2, a tube 3, and an inner structure 5 are configured to be individually curved by being elastically deformed according to the shape of the restriction member 4. Naturally, the sheath 2, the tube 3, and the inner structure 5 may individually be curved in a natural state.

According to this tissue separation device 1, similar effects to those of the aforementioned first embodiment can be obtained.

Because the tissue separation device 1 has a part that is curved in a circular arc shape, a puncture hole extending from a body surface and passing an obturator foramen of a pelvis to reach a region between a urethra and a vagina can be relatively easily formed.

While the curved shape in the tissue separation device 1 in this embodiment is a circular arc, is the invention is not limited in this regard. For example, the curved shape may be an elliptic arc or the like.

While the tissue separation device disclosed here has been described above on the basis of the illustrated embodiments representing examples of the invention, the present invention is not limited to the embodiments, and the configuration of each part can be replaced with an arbitrary configuration that has a similar function. Also, other arbitrary structures may be added to the present invention.

In addition, the present invention may be a combination of arbitrary two or more configurations (features) of the above embodiments.

While the number of the wires constituting the expansion part is two in the above embodiments, the number of wire(s) in the present invention may be one or may be three or more.

Further, in the present invention, the wire may be so configured as to be rotatable about its axis. In this case, by rotating the wires in an expanded state, it is possible to dissect a biological tissue largely.

In addition, while the expansion part is the wires in the above embodiments, the expansion part in the present invention is not restricted to the wires, but may be, for example, a flexible tubular body formed with a plurality of slits in a side portion of the tubular body. In this case, the slits each extend in the longitudinal direction of the tubular body, and are arranged to be juxtaposed in the circumferential direction. At the time of expanding the expansion part, a distal portion and a proximal portion of the tubular body are brought closer to each other. As a result, bar-like portions extending in the longitudinal direction of the tubular body are curved, and are expanded.

It is also possible that the expansion part may be a balloon which can be expanded and contracted. A restriction member having slits for restricting the expansion direction of the balloon may be provided in the vicinity of the outer circumference of the balloon. In this case, the balloon protrudes through the slits at the time of expansion.

Further, while the expansion part is provided at a distal portion of the inner structure in the above embodiments, the invention is not limited in this way. The expansion part may, for example, be provided at an intermediate portion of the inner structure.

The outer structure as a whole is elastically deformable in the above embodiments, but the invention is not limited in this way. For example, only the deformation part of the outer structure may be elastically deformable.

In addition, while the deformation part is elastically deformable in the above embodiments, this is not a limitation on the present invention. The deformation part may, for example, include a non-elastic body, and it may be in a folded form in a contracted state.

Further, the external shape in cross section of that part of the tissue separation device which is inserted into a living body may, for example, be a flat shape as the tissue separation device is viewed in the longitudinal direction of the device.

In addition, the external shapes in cross section of the tubular body 52, the fixation part 531 and the like may individually be, for example, tetragons, an ellipses or the like that can prevent rotation of the tubular body 52 and the fixation part 531.

The description above describes the tissue separation device for use in implanting an implantable implant for treatment of female urinary incontinence into a living body, but the use of the tissue separation device of the present invention is not limited to this described usage.

The tissue separation device in the examples disclosed here includes an inner structure including an expansion part which is expandable, and an operation unit which is disposed apart from the expansion part and which operates expansion of the expansion part and an outer structure disposed outside of the inner structure, the outer structure having a deformation part into which the expansion part is inserted, which deforms following up to a deformation of the expansion part and which is inserted into a living body, characterized in that the expansion part inserted in the deformation part and in an expanded state is moved relative to the deformation part without moving the deformation part relative to the living body.

The deformation part of the outer structure is continuously and gradually expanded along the longitudinal direction thereof, by moving the expansion part in an expanded state within the outer structure in relation to the outer structure, without moving the outer structure in relation to a living body. This makes it possible to dissect a biological tissue smoothly and with low invasion, thereby alleviating the burden on the patient. Accordingly, the tissue separation device of the present invention has industrial applicability.

The detailed description above describes a tissue separation device. The invention is not limited, however, to the precise embodiments and variations described. Various changes, modifications and equivalents can be employed by one skilled in the art without departing from the spirit and scope of the invention as defined in the accompanying claims. It is expressly intended that all such changes, modifications and equivalents which fall within the scope of the claims are embraced by the claims.

What is claimed is:

1. A tissue separation device comprising:
an inner structure including an expansion part which is expandable from a contracted state to an expanded state, and an operation unit which is disposed proximal to the expansion part and which is operable to expand the expansion part from the contracted state to the expanded state;
a restriction member comprising a tubular body with a lumen, the expansion part of the inner structure being positioned within the lumen of the tubular body when the expansion part is in the contracted state;
the tubular body of the restriction member comprising a slit which restricts an expansion direction of the expansion part when the expansion part expands so that the expansion part in the expanded state protrudes out through the slit in the tubular body of the restriction member;
an outer structure disposed outside of the restriction member, the outer structure including a deformation part covering the slit in the tubular body of the restriction member, the deformation part being deformed outwardly during expansion of the expansion part to the expanded state by virtue of the expansion part in the expanded state protruding out through the slit and outwardly deforming the deformation part, the deformation part being insertable into a living body; and wherein the expansion part in the expanded state in the deformation part is moved relative to the deformation part without moving the deformation part relative to the living body.

2. The tissue separation device according to claim 1, wherein the restriction member is disposed between the inner structure and the outer structure in a radial direction.

3. The tissue separation device according to claim 1, wherein the restriction member possesses a distal portion which comprises a needle body and a needle tip which punctures a biological tissue.

4. The tissue separation device according to claim 1, wherein the restriction member has an engaging part which engages with the outer structure and which inhibits the deformation part of the outer structure from moving distally relative to the restriction member.

5. The tissue separation device according to claim 1, wherein the restriction member is elongated in shape and has a portion curved along a longitudinal direction thereof.

6. The tissue separation device according to claim 1, wherein the inner structure has a holding part which holds a state where the expansion part is expanded.

7. The tissue separation device according to claim 1, wherein the expansion part has at least one wire and is so configured as to be expanded by curving of the wire causing the wire to protrude through the slit of the restriction member.

8. The tissue separation device according to claim 7, wherein the operation unit operates to effect flexure of the wire or wires by bringing a distal-side portion and a proximal-side portion of the wire toward each other.

9. The tissue separation device according to claim 1, wherein
the expansion part has two wires and is so configured as to be expanded by curving of the two wires such as to protrude in opposite directions,
the restriction member comprises a second slit positioned opposite the slit in the circumferential direction, and
the two wires protruding through the slit and the second slit in opposite directions when the expansion part is in the expanded state.

10. The tissue separation device according to claim 1, wherein the deformation part is elastically deformable.

11. The tissue separation device according to claim 1, comprising an outer tube in which the outer structure is positioned.

12. The tissue separation device according to claim 1, wherein the expansion part comprises at least one wire expandable from the contracted state to the expanded state through operation of the operation unit, the expansion of the at least one wire causing the at least one wire to contact the deformation part of the outer structure and outwardly expand the deformation part of the outer structure into pressing contact with tissue of the living body.

13. The tissue separation device according to claim 12, wherein the restriction member is positioned in surrounding relation to the at least one wire when the at least one wire is in the contracted state so that the restriction member is positioned radially between the at least one wire in the contracted state and the deformation part of the outer structure.

14. The tissue separation device according to claim 1, wherein the operation unit is operable to move axially, and the expansion part comprises at least one wire expandable from the contracted state to the expanded state as a result of axial movement of the operation unit, the inner structure including a shaft connected to and movable together with the operation unit, the at least one wire being fixed to a part at a distal end portion of the shaft so that the axial movement of the shaft in a proximal direction as a result of operation of the operation unit causes the at least one wire to expand outwardly through the slit of the restriction member into contact with the deformation part.

15. The tissue separation device according to claim 1, wherein the restrictive member comprises a second slit, the inner structure includes a shaft connected to and movable together with the operation unit, the expansion part including a pair of wires each possessing a distal end connected to a part at a distal end of the shaft so that axial movement of the shaft in a proximal direction as a result of operation of the operation unit causes the pair of wires to expand radially outwardly through the slit and the second slit in diametrically opposite directions into contact with the deformation part.

16. A tissue separation device for separating tissue in a living body, the tissue separation device comprising:
an outer sheath comprising a lumen;
an elastically deformable tube positioned in the lumen of the outer sheath, the outer sheath being movable in an axial direction relative to the elastically deformable tube, the elastically deformable tube comprising a lumen and possessing an inner wall surface;
a tubular restriction member positioned in the lumen of the elastically deformable tube, the tubular restriction member comprising a lumen;
an elongated inner member comprising an expansion wire, the elongated inner member, inclusive of the expansion wire, being positioned in the lumen of the tubular restriction member;
an operation member operatively connected to the expansion wire and operable to expand the expansion wire from a contracted state to an expansion state, the expansion wire being entirely within the lumen of the tubular restriction member when the expansion wire is in the contracted state and the expansion wire protruding radially outward beyond the tubular restriction member to contact the inner wall surface of the elastically deformable tube to deform the elastically deformable tube radially outwardly when the expansion wire is in the expansion state; and
the expansion wire being movable in the axial direction relative to the restriction member and the elastically deformable tube without moving the elastically deformable tube in the axial direction relative to the living body.

17. The tissue separation device according to claim 16, wherein the tubular restriction member comprises a slit through which the expansion wire protrudes when the expansion wire is in the expanded state, the slit restricting an expansion direction of the expansion wire when the expansion wire expands to protrude through the slit of the restriction member to contact and deform the elastically deformable tube.

18. The tissue separation device according to claim 16, wherein the tubular restriction member comprises a needle tip at a distal-most end of the tubular restriction member.

19. A method comprising:
puncturing body tissue of a living body with a tissue separation device, the tissue separation device comprising a needle that punctures the body tissue, the tissue separation device further comprising an elastically deformable outer tube, an elongated restriction member, and an elongated inner member, the restriction member being positioned in a lumen of the outer tube during the puncturing of the body tissue, and the inner member being positioned in a lumen of the restriction member during the puncturing of the body tissue, the outer tube possessing an inner wall surface and an outer wall surface, the restriction member possessing a slit, and the inner member comprising a wire;

expanding the wire of the inner member so that the wire extends radially outwardly through the slit of the restriction member and contacts the inner wall surface of the outer tube to radially outwardly expand the outer wall surface of the outer tube into contact with a first area of the body tissue; and moving the inner member relative to the outer tube while the wire is expanded and in contact with the inner wall surface of the outer tube to cause the outer wall surface of the outer tube to contact a second area of the body tissue spaced from the first area, the outer tube not moving in an axial direction relative to the body tissue while the inner tube is being moved.

20. The method according to claim 19, wherein the wire of the inner member remains within the outer tube at all times while the tissue separation device is in the living body, such that the wire of the inner member does not communicate with fluids of the living body.

* * * * *